United States Patent
Meyer et al.

(10) Patent No.: US 9,066,714 B2
(45) Date of Patent: Jun. 30, 2015

(54) TISSUE STABILIZING DEVICE AND METHODS INCLUDING A SELF-EXPANDABLE HEAD-LINK ASSEMBLY

(71) Applicant: Medtronic, Inc., Minneapolis, MN (US)

(72) Inventors: Eric Meyer, Andover, MN (US); Jeffrey Sandstorm, Forest Lake, MN (US); Robert Reetz, Rockford, MN (US); Eric Fox, Prior Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/914,129

(22) Filed: Jun. 10, 2013

(65) Prior Publication Data

US 2013/0274547 A1    Oct. 17, 2013

Related U.S. Application Data

(63) Continuation of application No. 12/846,147, filed on Jul. 29, 2010, now Pat. No. 8,460,172.

(51) Int. Cl.
| | |
|---|---|
| *A61F 13/00* | (2006.01) |
| *A61B 17/02* | (2006.01) |
| *A61B 17/29* | (2006.01) |

(Continued)

(52) U.S. Cl.
CPC ..... *A61B 17/0206* (2013.01); *A61B 2017/0237* (2013.01); *A61B 2017/0243* (2013.01); *A61B 2017/2905* (2013.01); *A61B 2017/306* (2013.01); *A61B 2017/308* (2013.01); *A61B 2019/268* (2013.01)

(58) Field of Classification Search
CPC ............ A61B 2017/0243; A61B 2017/00243; A61B 17/02; A61B 17/0206; A61B 17/0218

USPC ............................. 600/37, 201–234; 606/205
See application file for complete search history.

(56) References Cited

U.S. PATENT DOCUMENTS

| | | |
|---|---|---|
| 3,096,962 A | 7/1963 | Meijiis |
| 4,949,927 A | 8/1990 | Madocks et al. |

(Continued)

FOREIGN PATENT DOCUMENTS

| | | |
|---|---|---|
| WO | WO01/17437 | 3/2001 |
| WO | WO2007/127818 | 11/2007 |
| WO | WO 2007127818 A2 * | 11/2007 |

OTHER PUBLICATIONS

PCT/US2011/044876 PCT International Search Report and Written Opinion.

*Primary Examiner* — Charles A Marmor, II
*Assistant Examiner* — Eileen Hyde

(57) ABSTRACT

A tissue stabilizer including an elongated arm, a collet, and a head-link assembly. The collet is disposed at a distal end of the arm. The head-link assembly includes a tube and a spreading mechanism. The tube forms an intermediate section and opposing arms each terminating at a tip. The spreading mechanism can adjust a lateral distance between the tips, and includes first and second articulating members each having a leg and a collet interface body. The first member further includes a female hinge feature, whereas the second member includes a male hinge feature differing from the female hinge feature. The legs of are mounted to discrete regions of the tube, and the male hinge feature is pivotably coupled to the female hinge feature. Automatic spreading of a lateral distance between the tips occurs in response to a compressive force applied to the collet interface bodies.

14 Claims, 22 Drawing Sheets

(51) Int. Cl.
   *A61B 17/30* (2006.01)
   *A61B 19/00* (2006.01)

(56) References Cited

U.S. PATENT DOCUMENTS

| | | | |
|---|---|---|---|
| 5,348,259 A | 9/1994 | Blanco et al. | |
| 5,380,338 A * | 1/1995 | Christian | 606/130 |
| 5,513,827 A | 5/1996 | Michelson | |
| 5,727,569 A | 3/1998 | Benetti et al. | |
| 5,749,892 A | 5/1998 | Vierra et al. | |
| 5,836,311 A | 11/1998 | Borst et al. | |
| 5,876,332 A | 3/1999 | Looney | |
| 5,899,425 A | 5/1999 | Corey Jr. et al. | |
| 5,927,284 A | 7/1999 | Borst et al. | |
| 5,947,896 A | 9/1999 | Sherts et al. | |
| 6,007,486 A | 12/1999 | Hunt et al. | |
| 6,013,027 A | 1/2000 | Khan et al. | |
| 6,015,378 A | 1/2000 | Borst et al. | |
| 6,019,722 A | 2/2000 | Spence et al. | |
| 6,019,772 A | 2/2000 | Shefaram et al. | |
| 6,036,641 A | 3/2000 | Taylor et al. | |
| 6,102,853 A | 8/2000 | Scirica et al. | |
| 6,113,534 A | 9/2000 | Koros et al. | |
| 6,152,874 A | 11/2000 | Looney et al. | |
| 6,193,652 B1 | 2/2001 | Berky et al. | |
| 6,264,605 B1 | 7/2001 | Scrica et al. | |
| 6,328,688 B1 | 12/2001 | Borst et al. | |
| 6,334,843 B1 | 1/2002 | Borst et al. | |
| 6,336,898 B1 | 1/2002 | Borst et al. | |
| 6,350,229 B1 | 2/2002 | Borst et al. | |
| 6,364,826 B1 | 4/2002 | Borst et al. | |
| 6,371,906 B1 | 4/2002 | Borst et al. | |
| 6,394,948 B1 | 5/2002 | Borst et al. | |
| 6,394,951 B1 | 5/2002 | Taylor et al. | |
| 6,447,443 B1 | 9/2002 | Keogh et al. | |
| 6,464,629 B1 | 10/2002 | Boone et al. | |
| 6,464,630 B1 | 10/2002 | Borst et al. | |
| 6,506,149 B2 | 1/2003 | Peng et al. | |
| 6,565,508 B2 | 5/2003 | Scirica et al. | |
| 6,709,389 B2 | 3/2004 | Farascioni | |
| 6,733,445 B2 | 5/2004 | Sherts et al. | |
| 6,752,759 B2 | 6/2004 | Martin et al. | |
| 6,758,808 B2 | 7/2004 | Paul et al. | |
| 6,849,044 B1 | 2/2005 | Voss et al. | |
| 6,899,670 B2 | 5/2005 | Peng et al. | |
| 7,201,716 B2 | 4/2007 | Boone et al. | |
| 2001/0025905 A1 | 10/2001 | Carpenter et al. | |
| 2001/0037123 A1 | 11/2001 | Hancock | |
| 2002/0111537 A1* | 8/2002 | Taylor et al. | 600/210 |
| 2002/0115911 A1 | 8/2002 | Knight et al. | |
| 2003/0216619 A1 | 11/2003 | Scirica et al. | |
| 2004/0002625 A1 | 1/2004 | Dietz et al. | |
| 2004/0030223 A1 | 2/2004 | Calafiore et al. | |
| 2004/0171917 A1 | 9/2004 | Paul et al. | |
| 2004/0176659 A1 | 9/2004 | Peng et al. | |
| 2004/0267097 A1 | 12/2004 | Xiao et al. | |
| 2007/0123747 A1 | 5/2007 | Boone et al. | |
| 2007/0208223 A1 | 9/2007 | Julian et al. | |
| 2008/0108878 A1 | 5/2008 | Goodman et al. | |
| 2008/0139879 A1 | 6/2008 | Olson et al. | |
| 2009/0082620 A1* | 3/2009 | Haarstad et al. | 600/37 |
| 2009/0137865 A1 | 5/2009 | Green, II et al. | |
| 2010/0317925 A1 | 12/2010 | Banchieri et al. | |

* cited by examiner

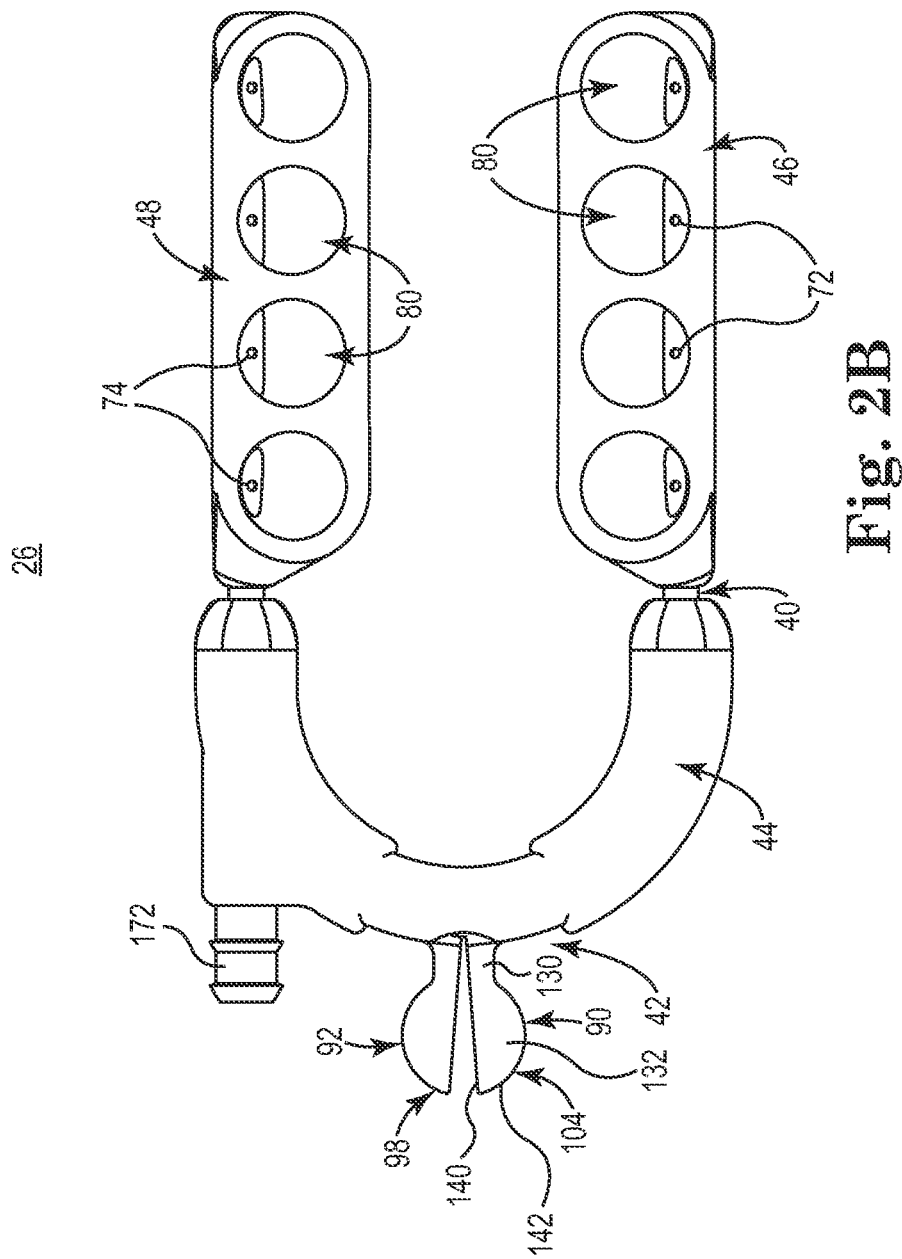

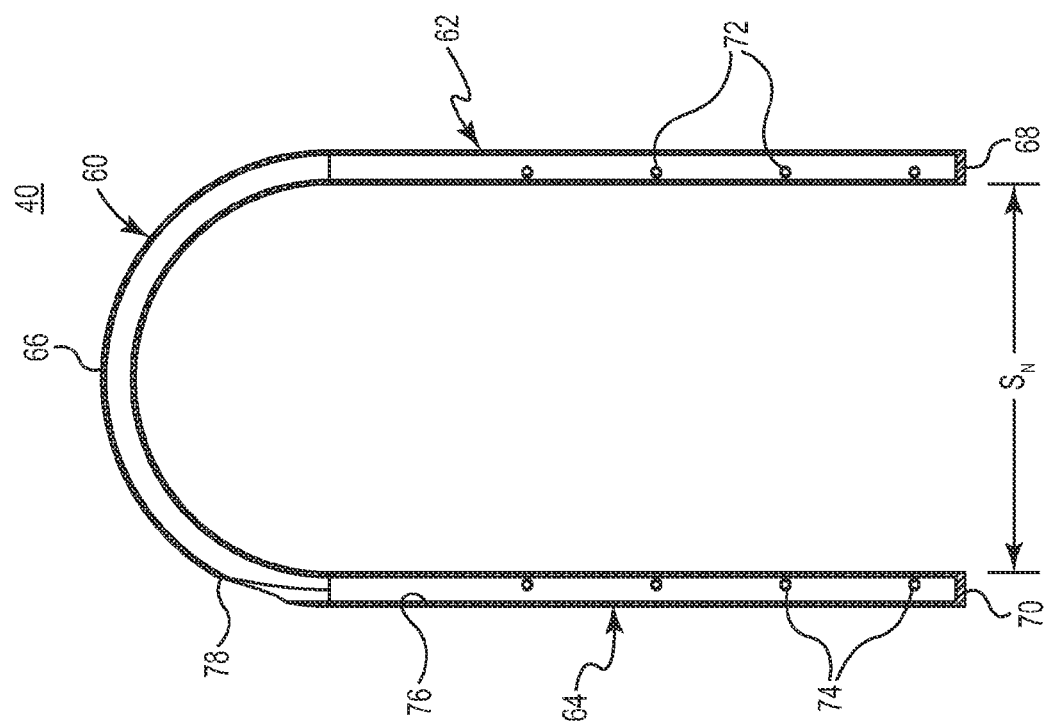

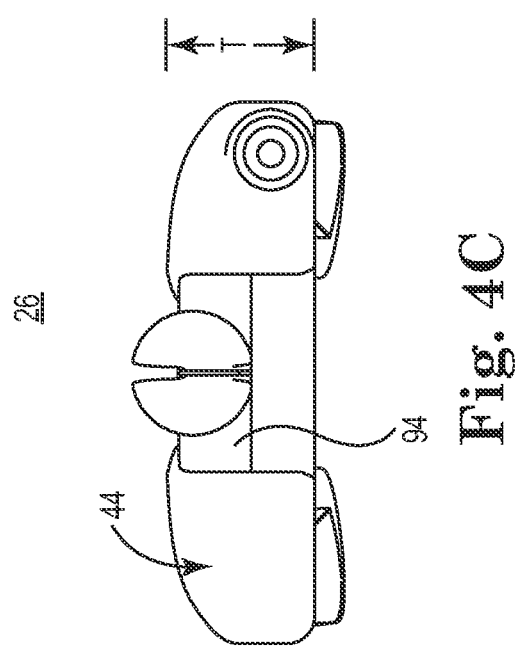

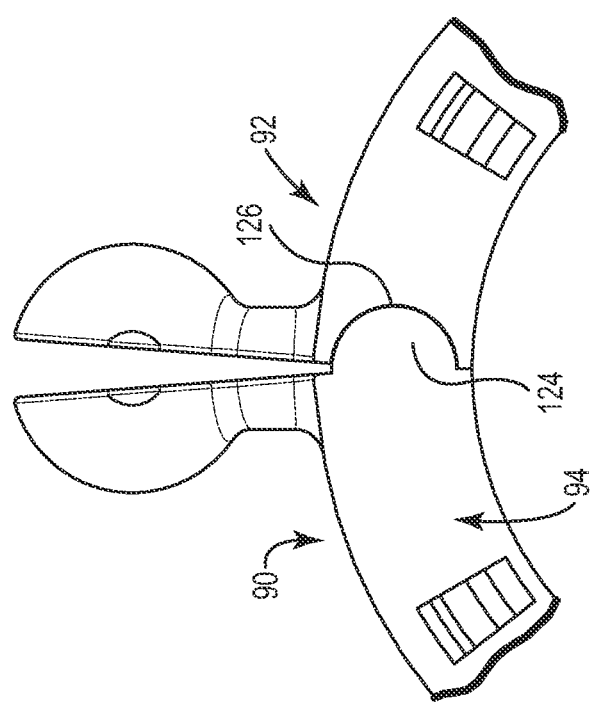

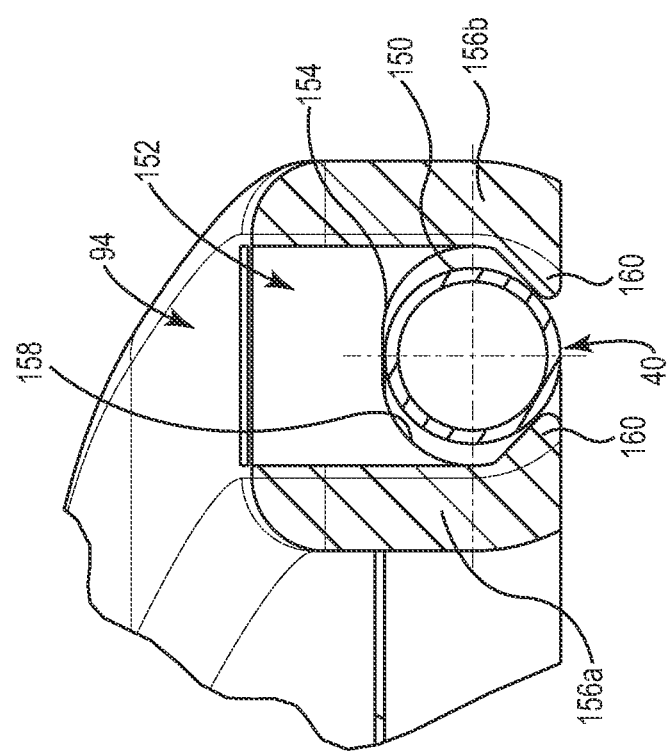

TISSUE STABILIZING DEVICE AND METHODS INCLUDING A SELF-EXPANDABLE HEAD-LINK ASSEMBLY

RELATED APPLICATIONS

This application is a Continuation of and claims the benefit of U.S. patent application Ser. No. 12/846,147 filed Jul. 29, 2010, now allowed, the disclosure of which is herein incorporated by reference in its entirety.

BACKGROUND

The present disclosure generally relates to surgery on body tissues and organs. More particularly, the present disclosure relates to devices and methods for engaging tissue of an organ, for example for positioning an organ in a desired orientation or for temporarily immobilizing a local area of tissue subject to motion, such as the heart wall, which permits a surgical procedure to be performed on that local area of tissue.

Approximately 300,000 patients in the United States undergo coronary artery bypass grafting operations every year. Conventional coronary artery bypass graft operations require the beating of the heart be ceased during the procedure. A heart-lung machine is used to pump and oxygenate the patient's blood while the heart is stopped. More recently, off-pump surgery, or beating heart surgery, has become an attractive alternative to traditional heart-lung machine procedures.

One challenge in beating heart coronary artery bypass graft surgery is that it can be difficult to suture or sew on a beating heart. The surgeon must use a "stabilization" system to keep the heart steady. The stabilization system typically consists of a heart positioner and a tissue stabilizer. The heart positioner guides and holds the heart in a position that provides best access to blocked arteries. The tissue stabilizer holds a small area of the heart stationary while a surgeon attaches a transplanted vessel around blockages in one or more coronary arteries, providing the surgeon with an unimpeded view of the stabilized suture site.

Some tissue stabilizers are designed to immobilize epicardial tissue in the immediate vicinity of an anastomosis site through a pressure-type stabilizer employing a simple mechanical fork. Such a device stabilizes the heart by pressing the fork downwards onto the heart surface. The fork is typically mounted to an elongated arm, which in turn is typically mounted to a retractor holding the patient's ribs apart to create an operative window. Angular movement of the arm relative to the retractor in some cases is accomplished by means of a turret, which may be clamped in a desired rotational position. Longitudinal movement of the arm relative to the retractor is typically allowed as well, and clamping mechanisms are typically provided to allow clamping of the arm to the turret and locking of the fork relative to the arm. Exemplary pressure tissue stabilization devices are disclosed in U.S. Pat. Nos. 6,036,641 and 6,876,332.

More recently, suction-based tissue stabilizers have gained wide-spread acceptance, such as the Medtronic Octopus® Tissue Stabilizer (available from Medtronic, Inc.), and employ a comparatively long, flexible, articulating arm carrying a pair of suction paddles or pods at its distal end. The suction pods are fluidly connected to a source of negative pressure. During use, the arm is typically secured to a retractor holding the patient's ribs apart to create an operative window. The pods are placed on opposite sides of the anastomosis site, and suction is applied to grip and immobilize the surface of the heart. Thereafter, tension is applied along the length of the arm to lock the arm in a desired spatial orientation and to lock the position of the pods relative to the arm. Examples of such devices are described in U.S. Pat. Nos. 6,464,629 and 6,866,628, the entire teachings of both of which are incorporated herein by reference. Other examples of suction-type tissue stabilizers are described in U.S. Pub. No. 2008/0139879 entitled "Methods and Devices for Stabilizing Tissue", incorporated herein by reference in its entirety. With these devices, the suction-applying pods are carried by a generally Y-shaped head provided as part of head-link assembly that is rotatably coupled to a collet carried by the articulating arm. With these constructions, a tension element is operable by the surgeon to selectively clamp a spherical base of the head-link assembly relative to the collet. Upon loosening of the tension element, the head-link assembly can be rotated and/or pivoted at virtually any angle (i.e., yaw, pitch, and roll) above a plane perpendicular the collet, promoting multiple device positions including what is commonly referred to as pods-up, pods-down, and pods-to-the-side applications. Examples of such suction tissue stabilizers are available from Medtronic, Inc. under the trade name Octopus® Evolution™ Tissue Stabilizer.

Although available tissue stabilizers for use with off-pump coronary artery bypass graft surgical procedures are highly viable, any improvements will be well-accepted. For example, surgeons desire the ability to slightly stretch tissue of the heart between the suction pods of the tissue stabilizer, and may prefer to accomplish spreading of the pods without directly handling the head-link assembly.

SUMMARY

Some aspects in accordance with principles of the present disclosure relate to a tissue stabilizer including an elongated arm, a collet, and a head-link assembly. The elongated arm terminates at a distal end. The collet is disposed at the distal end. Finally, the head-link assembly is rotatably coupleable to the collet and includes a tube and a spreading mechanism. The tube is configured to apply negative pressure to tissue, and forms an intermediate section, a first arm, and a second arm. The first arm extends from the intermediate section and terminates at a tip. The second arm also extends from the intermediate section and terminates at a tip, but is opposite (e.g., laterally spaced from) the first arm. The spreading mechanism is configured to adjust a lateral distance between the tips and includes first and second articulating members. Each of the articulating members includes a leg and a collet interface body projecting from the leg. The first articulating member further includes a female hinge feature, whereas the second spreading member includes a male hinge feature differing in shape from the female hinge feature. Upon final construction of the head-link assembly, the legs of the spreading mechanism are mounted to discrete regions of the intermediate section of the tube, respectively, and the male hinge feature is pivotably coupled with the female hinge feature. The head-link assembly is transitionable from a natural state having a first lateral distance between the tips to an expanded state having a second lateral distance between the tips in response to a compressive force applied to the collet interface bodies. In this regard, the first lateral distance is less than the second lateral distance. For example, when the collet interface bodies are inserted within the collet and the collet is tightened, the collet interface bodies are forced toward one another, causing the articulating member legs to pivot relative to one another. This pivot force, in turn, is transferred to the tube, causing the first and second arms to spread apart. In some embodiments, the tube is U-shaped, with the intermediate section defining a curvature having a mid-point. In related embodiments, the hinge features are coupled to one another at the mid-point, and the collet interface bodies are generally aligned with the mid-point. In other embodiments, the head-link assembly further includes a polymer encapsulating body over-molded to the tube and the spreading mechanism in a manner permitting desired articulation of the hinge features. In yet other embodiments, the tube forms a single lumen extending along and between the opposing arms for supplying negative pressure to vacuum orifices formed in the arms; this single lumen is fluidly connected to a source of negative pressure via a single inlet formed through a thickness of the intermediate section.

Yet other aspects in accordance with principles of the present disclosure relate to a tissue stabilizer including an elongated arm, a collet, and a head-link assembly. The elongated arm terminates at a distal end at which the collet is disposed. The head-link assembly is rotatably coupleable to the collet and includes a tube and a spreading mechanism. The tube is adapted to apply negative pressure to tissue and defines an exterior surface and a lumen. Further, the tube forms an intermediate section and opposing, first and second arms extending from the intermediate section each terminating at a tip. The spreading mechanism is formed apart from the tube, and is mounted to the exterior surface thereof. The spreading mechanism includes first and second articulating members each having a leg, a collet interface body, and a hinge feature. Upon assembly of the spreading mechanism to an exterior surface of the tube, the legs are mounted to the intermediate section, the hinge features are pivotably coupled to one another, and the collet interface bodies are aligned. The head-link assembly is transitionable from a natural state having a first lateral distance between the tips to an expanded state having a second lateral distance between the tips in response to a compressive force imparted upon the collet interface bodies. In this regard, the first lateral distance is less than the second lateral distance. By forming the spreading mechanism apart from the negative pressure supply tube, the head-link assembly provides an automated spread feature that is simplistic, low profile, robust, reliable, and easy to manufacture.

Yet other aspects in accordance with principles of the present disclosure relate to a method for stabilizing tissue. The method includes clamping a tissue stabilizer to a retractor. The tissue stabilizer includes a collet disposed at a distal end of the elongated arm, as well as a head-link assembly rotatably coupled to the collet. The head-link assembly includes a tube defining an intermediate section and opposing, first and second arms extending from the intermediate section. Further, a spreading mechanism is provided with the head-link assembly and includes first and second articulating members each having a leg and a collet interface body projecting from the leg. The first articulating member further includes a female hinge feature, and the second articulating member further includes a male hinge feature differing in shape from the female hinge feature. The legs are mounted to discrete regions of the intermediate section, respectively, and the male hinge feature is pivotably coupled to the female hinge feature. The head-link assembly is rotated and pivoted relative to the collet to position the head-link assembly, in a natural state, against tissue. A vacuum is applied to the head-link assembly to create a suction force at the first and second arms to secure the arms to the tissue. A compressive force is applied to the collet interface bodies, causing the arms to spread apart from the natural state to an expanded state in order to stretch a portion of the tissue. In some embodiments, the tissue stabilizer further includes a tension element extending through the arm and coupled to the collet. In related embodiments, the compressive force is applied to the collet interface bodies by operating the tension element to tighten the collet over the collet interface bodies.

BRIEF DESCRIPTION OF THE DRAWINGS

FIG. 2B is a bottom plan view of the head-link assembly of FIG. 2A;

FIG. 3 is a cross-sectional view of a tube component of the head-link assembly of FIG. 2A;

FIG. 4C is a end view of the head-link assembly of FIG. 2A;

FIG. 6B is a bottom view of a portion of the spreading mechanism of FIG. 5 upon final assembly;

FIG. 7B is an enlarged end cross-sectional view of a portion of the head-link assembly of FIG. 7A, illustrating a clip component;

DETAILED DESCRIPTION

Figure 1:
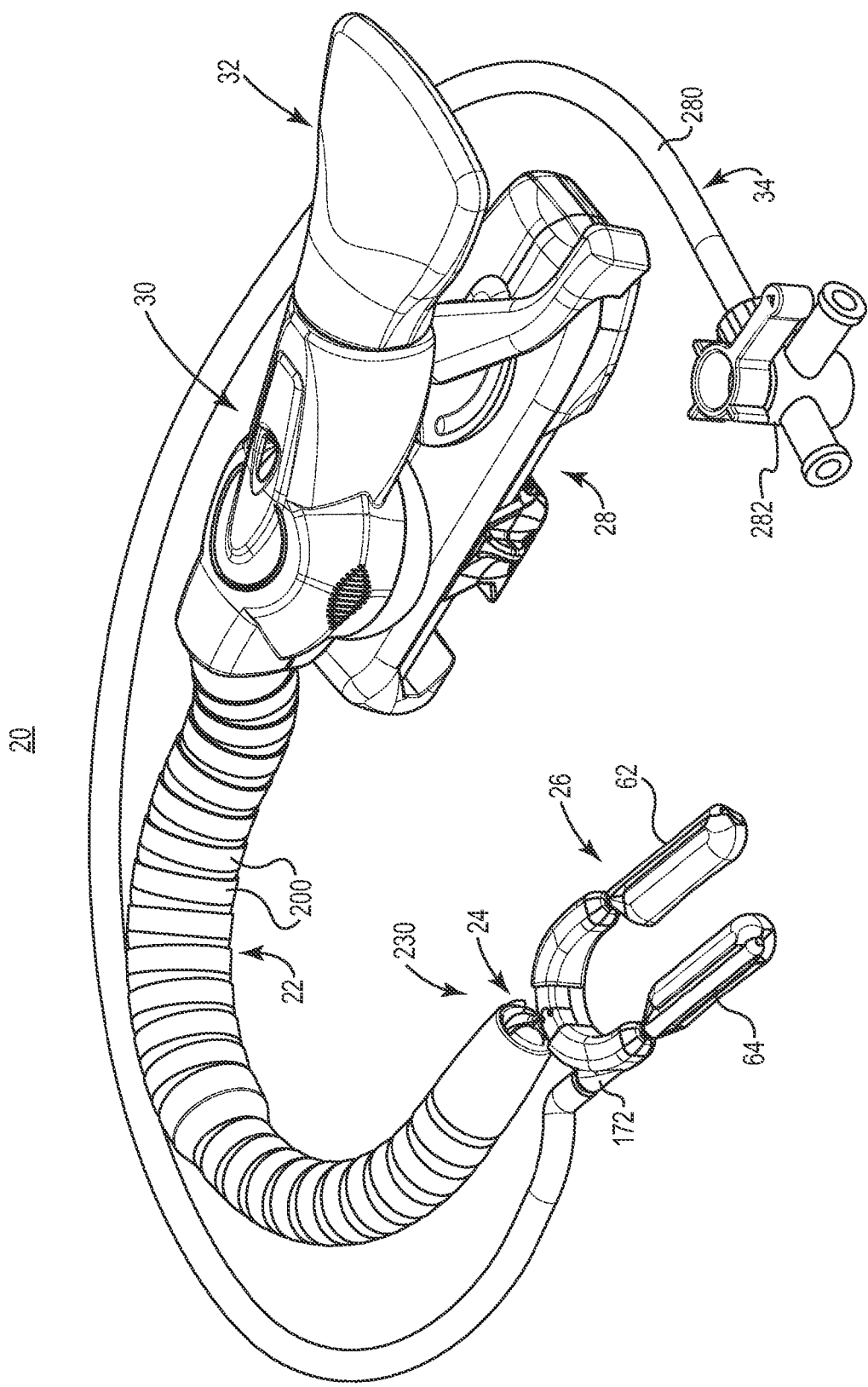
FIG. 1 is a perspective view of a tissue stabilizer in accordance with principles of the present disclosure.

One embodiment of a tissue stabilizer 20 in accordance with principles of the present disclosure and for use in stabilizing tissue of a bodily organ, such as the heart, during a surgical procedure is shown in FIG. 1. The tissue stabilizer 20 includes an elongated arm 22, a collet 24, and a head-link assembly 26. Additional, optional components can also be included with the tissue stabilizer 20, such as a clamp 28, a turret 30, a handle 32, and/or a vacuum tube assembly 34. Details on the various components are provided below. In general terms, however, the collet 24 is disposed at a distal end of the elongated arm 22. The head-link assembly 26 is configured to apply negative pressure to contacted tissue (e.g., via the vacuum tube assembly 34), and is rotatably coupleable to the collet 24. In this regard, the head-link assembly 26 can be rotatably and pivotally articulated relative to the collet 24 to a plethora of different angular orientations and rotational positions (e.g., freedom of motion in terms of yaw, pitch, and roll) relative to the collet 24. Further, the head-link assembly 26 is configured to effectuate an "automatic" spreading movement in which arms of the head-link assembly 26 are caused to self-transition to different lateral spacings. The terms "automatic spreading" and "automated spreading" are in reference to the arms of the head-link assembly transitioning from a natural lateral spacing to an expanded lateral spacing without the surgeon directly or physically handling the arms. Thus, the head-link assembly 26 can be spatially arranged as desired by the surgeon, and can quickly stretch contacted tissue as part of a surgical procedure.

Features of the various components 22-34 reflected in FIG. 1 and described below can be modified or replaced with differing structures and/or mechanisms. Thus, the present disclosure is in no way limited to the elongated arm 22, the collet 24, the clamp 28, the turret 30, etc., as shown and described below. More generally, tissue stabilizers in accordance with the present disclosure incorporate the head-link assembly 26 as described below in combination with a collet construction adapted to rotatably and pivotably maintain the head-link assembly 26 in a manner permitting operator-prompted, automated spreading of the head-link assembly 26.

Figure 2A:
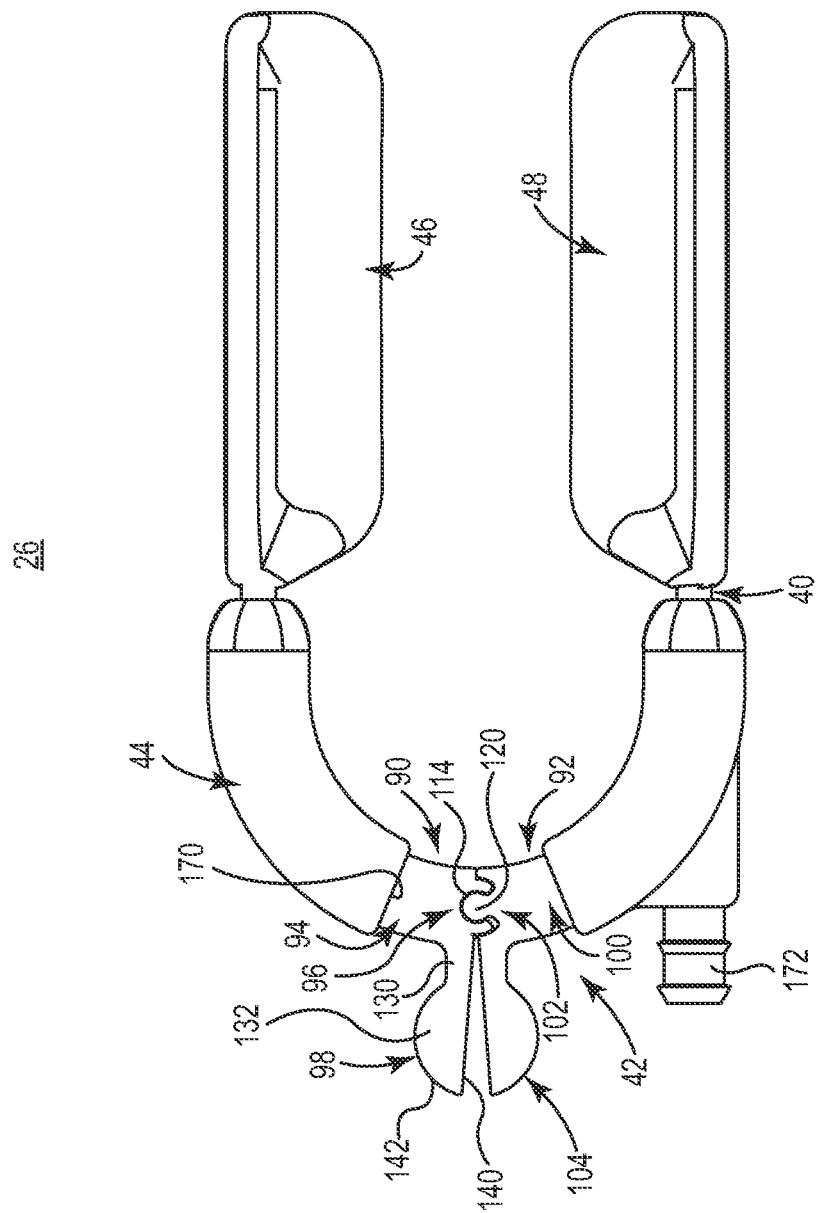
FIG. 2A is a top plan view of a head-link assembly component of the tissue stabilizer of FIG. 1.

The head-link assembly 26 is shown in greater detail in FIGS. 2A and 2B, and includes a negative pressure supply tube 40 (primarily hidden in the views of FIGS. 2A and 2B, and referenced generally), a spreading mechanism 42, an optional encapsulating body 44, and optional first and second pod bodies 46, 48. The pod bodies 46, 48 are carried by the tube 40 as shown, and include features fluidly connected to one or more lumens defined by the tube 40. The spreading mechanism 42 is assembled to the tube 40, and is constructed to cause deflection of the tube 40 in response to an external force (e.g., compressive force). The encapsulating body 44, where provided, better ensures a robust connection between the spreading mechanism 42 and the tube 40 in a manner permitting pivoting of the spreading mechanism 42 as described below.

The tube 40 is shown in simplified, cross-sectional form in FIG. 3 and can have a generally U-like shape to define an intermediate section 60, and opposing first and second arms 62, 64. With embodiments in which the tube 40 has a U-shape, the intermediate section 60 defines a curvature having a relatively uniform radius and defining a mid-point or apex 66. The first arm 62 extends from the intermediate section 60 and terminates a tip 68. The second arm 64 similarly extends from the intermediate section 60 and terminates at a tip 70. As shown, the arms 62, 64 are opposite one another in extension from the intermediate section 60, with the tips 68, 70 being laterally separated from one another by a lateral distance or spacing. In some constructions, the first and second arms 62, 64 are co-planar with one another and the intermediate section 60. Other shapes and/or orientations of the arms 62, 64 relative to the intermediate section 60 are also envisioned.

The tube 40 is formed of a material adapted to maintain a structural integrity of the tube 40 in the presence of expected vacuum pressures and deflection forces. In some embodiments, the tube 40 is a metal (e.g., stainless steel) or similar material that is somewhat malleable and has a shape memory characteristic. The shape memory characteristic causes the tube 40 to naturally assume the natural shape shown in FIG. 3 that defines a natural spacing $S_N$ between the tips 68, 70. When subjected to a deflection force, the arms 62, 64 can be displaced apart from one another (with the tube 40 effectively pivoting along the intermediate section 60, such as at the mid-point 66), increasing the lateral spacing between the tips 68, 70. Upon removal of this external force, however, the shape memory characteristic of the tube 40 causes the tube 40 to self-revert back toward the natural state having the natural lateral spacing $S_N$.

Each of the arms 62, 64 forms, in some constructions, a plurality of vacuum orifices 72, 74, respectively, through a wall thickness of the tube 40. The orifices 72, 74 are fluidly connected to one or more lumens 76 defined by the tube 40, with the orifices 72, 74 thus serving as conduits for applying negative pressure or suction delivered to the lumen(s) 76 onto tissue adjacent an exterior of the corresponding arms 62, 64. In some embodiments, the tube 40 forms a single, continuous lumen 76 that extends between the first and second arms 62, 64 and along the intermediate section 60. Negative pressure is delivered to the lumen 76 via an inlet or opening 78 defined along the intermediate section 60. An axis of the inlet 78 is parallel with the axis of the second arm 64, and in some embodiments is aligned with the axis of the second arm 64. Alternatively, in other embodiments, each of the arms 62, 64 can form a discrete lumen fluidly connectable to a source of negative pressure via a discrete inlet.

Returning to FIGS. 2A and 2B, where provided, the pod bodies 46, 48 are assembled to a respective one of the arms 62 or 64 as shown. The pod bodies 46, 48 can assume any variety of shapes, and generally include or form a plurality of pod cups 80 that are fluidly connected to respective ones of the corresponding orifices 72, 74 as best shown in FIG. 2B. The first and second pod bodies 46, 48 can be constructed of a material suitable for atraumatic tissue contact, such as polyurethane or polyvinylchloride, and can be over-molded onto the tube 40 or can be manufactured separately. Regardless, a negative pressure or vacuum applied to the lumen(s) 76 (FIG. 3) of the tube 40 is conveyed to the pod cups 80 via the corresponding orifices 72, 74 to effectuate application of a vacuum or suction force at each of the pod cups 80. In other embodiments, the pod bodies 46, 48 can have constructions differing from those reflected by the figures, and in yet other embodiments can be omitted.

The spreading mechanism 42 can be formed separately from, and subsequently assembled to, the tube 40. The spreading mechanism 42 includes a first articulating member 90 and a second articulating member 92. The first and second articulating members 90, 92 are, in some embodiments, nearly mirror images of each other apart from the differences noted below. As best shown in FIG. 2A, for example, the first articulating member 90 includes or defines a leg 94, a hinge feature 96, and a collet interface body 98. Similarly, the second articulating member 92 includes or forms a leg 100, a hinge feature 102, and a collet interface body 104. The legs 94, 100 can be generally identical, as can the collet interface bodies 98, 104. The hinge features 96, 102 are configured for pivotable engagement with one another, and thus can incorporate differing constructions as described below.

Figure 4A:
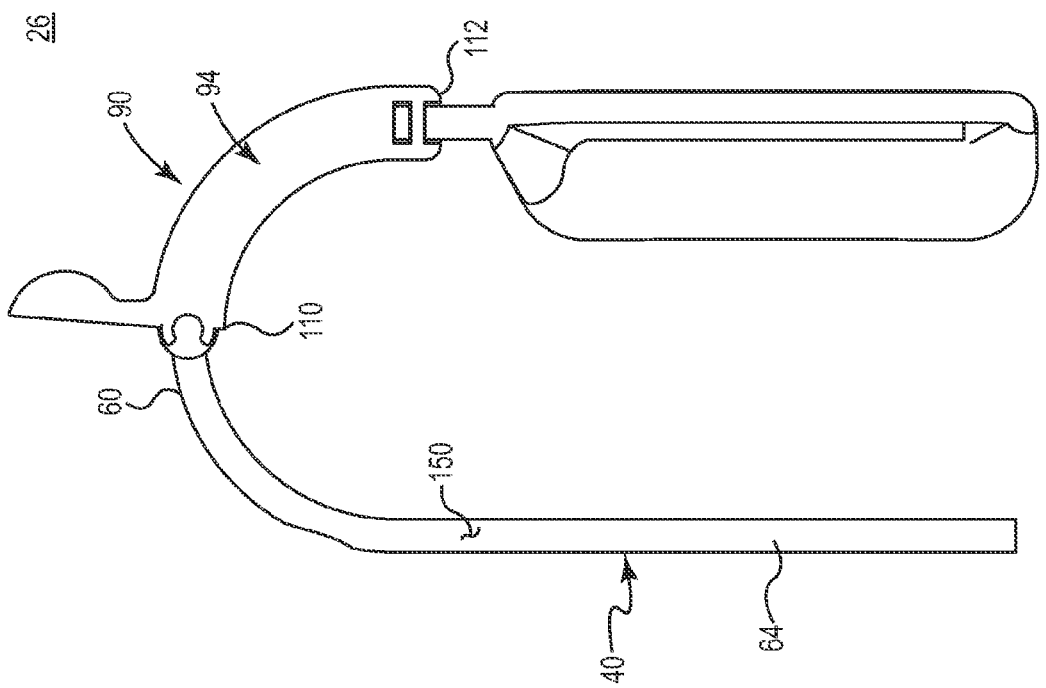
FIG. 4A is the top plan view of the head-link assembly of FIG. 2A with portions removed.
Figure 4B:
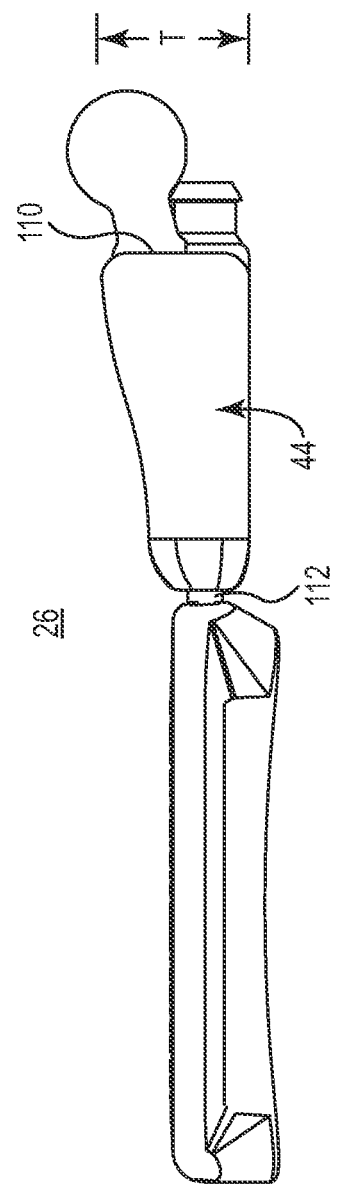
FIG. 4B is a side view of the head-link assembly of FIG. 2A.

As mentioned above, the legs 94, 100 can be identical, such that the following description of the leg 94 of the first articulating member 90 is equally applicable to the leg 100 of the second articulating member 92. As shown in FIG. 4A (that otherwise illustrates the head-link assembly 26 with the encapsulating body 44 (FIG. 2A), the second pod body 48 (FIG. 2A) and the second articulating member 92 (FIG. 2A) removed), the leg 94 extends from a first end 110 at which the hinge feature 96 is formed or provided to a second end 112 opposite the first end 110. In this regard, a shape of the leg 94 between the first and second ends 110, 112 generally corresponds with a shape or curvature of a corresponding region of the intermediate section 60 to which the leg 94 is mounted. The leg 94 defines a thickness in a plane perpendicular to a major plane of the tube 40 as reflected by the dimension T in FIGS. 4B and 4C (it being understood that in the views of FIGS. 4B and 4C, the encapsulating body 44 is shown and substantially covers the leg 94; however, an overall thickness T reflected in FIGS. 4B and 4C is representative of thickness variations in the leg 94). With cross-reference between FIGS. 4A-4C, the thickness T of the leg 94 tapers, in some constructions, from the first end 110 to the second end 112. Stated otherwise, the first end 110 has a thickness that is greater than a thickness of the second end 112. This tapering thickness generates a low profile attribute to the head-link assembly 26, providing enhanced visualization of the surgical site. In other embodiments, however, the leg 94 can have a more uniform thickness.

Figure 5:
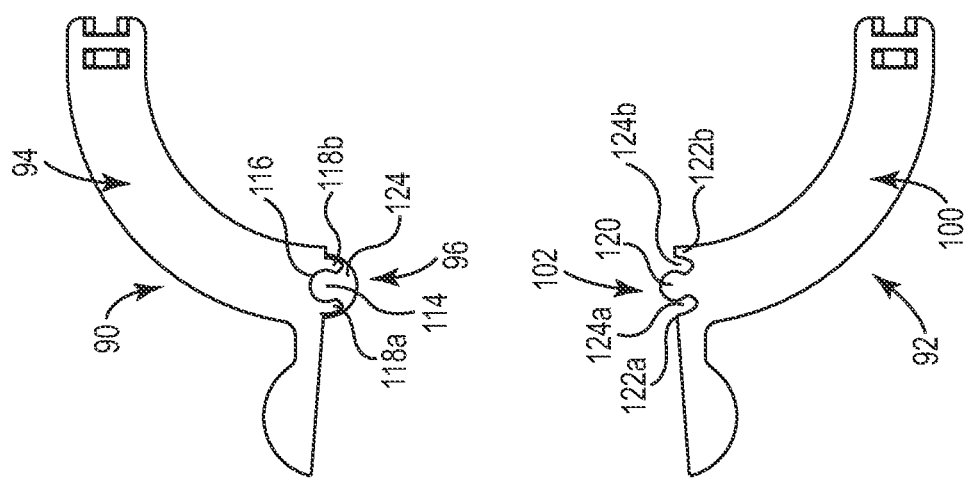
FIG. 5 is an exploded, top plan view of a spreading mechanism portion of the head-link assembly of FIG. 2A.

With reference to FIGS. 2A and 5, the hinge feature 96 is, in some embodiments, integrally formed by the leg 94 (at the first end 110) and can be a female hinge feature. With these constructions, the hinge feature 102 of the second articulating member 92 is a corresponding male hinge feature. For example, the female hinge feature 96 of the first articulating member 90 can include or define a slot or socket 114. The slot 114 has a curved or circular perimeter 116, and is bounded by opposing fingers 118a, 118b. The male hinge feature 102 of the second articulating member 92 includes or defines a pin 120 and opposing shoulders 122a, 122b. The pin 120 is separated from the shoulders 122a, 122b by channels 124a, 124b, respectively. The pin 120 has a generally rounded shape, and is sized to be rotatably received within the slot 114 (i.e., the rounded shape of the pin 120 generally matches a shape of the slot perimeter 116) to establish a pin-in-slot fulcrum. The fingers 118a, 118b slidably nest within the channels 124a, 124b, respectively, with the shoulders 122a, 122b serving to limit overt movement of the articulating members 90, 92 relative to one another. In some constructions, one or both of the shoulders 122a, 122b can be omitted. Further, a wide variety of other pivoting-type arrangements can be employed, with the hinge features 96, 102 assuming forms differing from those reflected in the FIGURES.

Figure 6A:
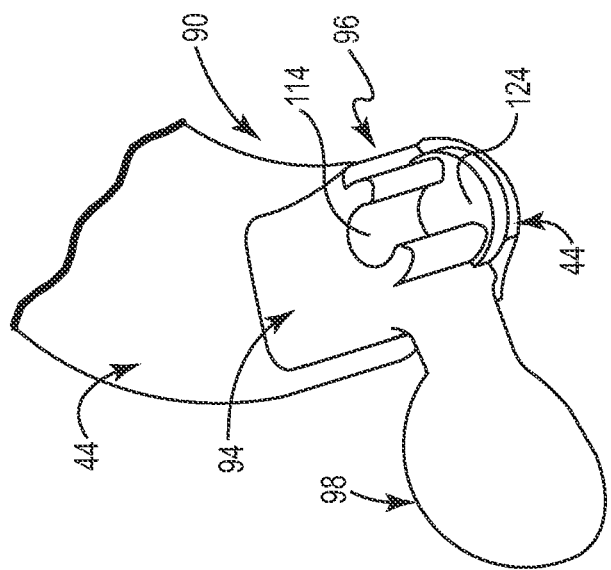
FIG. 6A is a perspective view of a portion of a first articulating member of the spreading mechanism of FIG. 5.

In addition to providing rotational stops, the fingers 118a, 118b and the shoulders 122a, 122b can serve to prevent introduction of material of the optional encapsulating body 44 (FIG. 2A) into a region of interface between the pin 120 and the slot 114 with embodiments in which the encapsulating body 44 is a plastic material over-molded to the articulating members 90, 92 (e.g., where the encapsulating body 44 is generated by molding a molten plastic about the articulating members 90, 92, the fingers 118a, 118b and the shoulders 122a, 122b obstruct the molten plastic from flowing or flashing between the pin 120 and the slot 114). Optionally, one or both of the articulating members 90, 92 can incorporate addition features that guard against undesirable plastic material flow into the pin 120/slot 114 region of the interface. For example, as best shown in FIGS. 6A and 6B, the first articulating member 90 can further include or form a guard plate 124 at the first end 110. The guard plate 124 is disposed at an end of the slot 114, and has a curved perimeter. The second articulating member 92 forms a corresponding groove 126. With additional reference to FIG. 2A, upon pivotable assembly of the pin 120 within the slot 114, the guard plate 124 is rotatably nested within the groove 126, effectively extending below the pin 120. Thus, the guard plate 124 shields an underside of the pin 120/slot 114 region of interface from flashing material of the encapsulating body 44 to better ensure desired pivoting of the pin-in-slot fulcrum.

Returning to FIGS. 2A and 2B, the collet interface bodies 98, 104 can be identical, with the following description of the collet interface body 98 of the first articulating member 90 applying equally to the collet interface body 104 of the second articulating member 92. The collet interface body 98 includes, in some embodiments, a neck 130 and a base 132. The neck 130 extends from the leg 94 at or adjacent the first end 110 (FIG. 4A) in a direction generally opposite the tube 40. The base 132, in turn, extends from the neck 130 opposite the leg 94, and provides an enlarged surface area (as compared to a surface area of the neck 130). In other constructions, the neck 130 can be omitted. Regardless, the collet interface body 98, and in particular the base 132, forms or defines an interior face 140 and an exterior face 142. The interior face 140 is flat, whereas the exterior face 142 is rounded. More particularly, the exterior face 142, at least along the base 132, can be approximately semi-spherical or semi-oval in shape. Upon arrangement of the collet interface bodies 98, 104 such that the interior faces 140 are in contact with one another, the exterior faces 142 combine to define a ball-like or sphere-like or near-sphere shape (e.g., the exterior faces 142 can combine to define a ball, an oval or football-type shape, etc.). Alternatively, other shapes are also envisioned.

The articulating members 90, 92 can each be integral, homogeneous bodies formed from a rigid material selected to maintain its integrity under expected forces. In some embodiments, the articulating members 90, 92 are each formed of an injection molded metal (e.g., steel), although other materials (e.g., ceramic) capable of providing the strength necessary in a small cross-section to bend open or spread the tube 40 during a spreading operation without yielding are also acceptable.

Figure 7A:
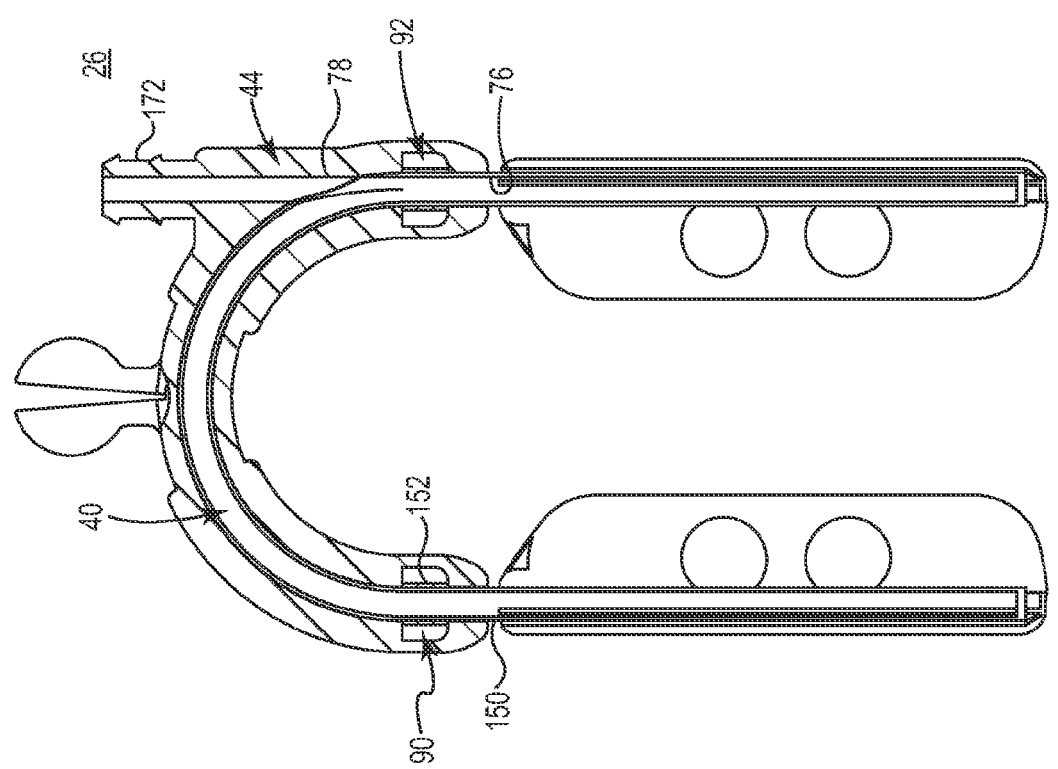
FIG. 7A is a cross-sectional view of the head-link assembly of FIG. 2A.

The articulating members 90, 92 can be assembled to the tube 40 in various manners. With constructions in which the spreading mechanism 42 is formed separately from the tube 40, the articulating members 90, 92 are mounted to an exterior 150 of the tube 40 as shown in FIGS. 4A and 7A. For example, the articulating members 90, 92 can be individually affixed to the exterior surface 150 by welds, adhesive, etc. Alternatively, each of the articulating members 90, 92 includes one or more clips 152 configured for assembly to the tube 40. FIG. 7B illustrates the clip 152 associated with the first articulating member 90 in greater detail, and reflects that a bottom surface 154 of the leg 94 can be relatively flat and generally faces (e.g., bears against) the exterior surface 150 of the tube 40. The clip 152 projects from the bottom surface 154 and includes opposing posts 156a, 156b that are laterally spaced from one another to define an aperture 158 sized to engage the tube 40. In some constructions, the posts 156a, 156b each terminate at a triangular-shaped end 160. When the tube 40 is inserted within the aperture 158, the triangular ends 160 press against the tube 40, effectively centering the tube 40 relative to the clip 152, and thus relative to a width of the leg 94. Other mounting techniques are also envisioned, such that the optional clip(s) 152 can assume other forms and/or can be omitted.

Returning to FIGS. 2A and 2B, to further enhance rigid mounting of the articulating members 90, 92 over (or to) the tube 40, the encapsulating body 44 can be incorporated. In general terms, the encapsulating body 44 is a plastic material over-molded to the tube 40 and the spreading mechanism 42, permanently encasing the components 40, 42 and negating the need for other bonding operations in some embodiments.

The encapsulating body 44 can be formed of an appropriate material (e.g., polyvinylchloride) exhibiting an appropriate durometer for atraumatic tissue contact (e.g., 85 Shore A), and is constructed or formed so as to not interfere with the hinge features 96, 102 or the collet interface bodies 98, 104. For example, the encapsulating body 44 can be molded in a manner defining a recess 170 (FIG. 2A) in a region at which the hinge features 96, 102 interface with one another and at which the collet interface bodies 98, 104 extend. To better ensure that the over-molded encapsulating body 44 does not flash or flow within the region of interface between the hinge features 96, 102, the optional shoulders 122a, 122b and/or guard plate 124 (FIG. 6A) can be provided as described above. Molding of the encapsulating body 44 can also include formation of a vacuum port 172 for connection to the vacuum tube assembly 34 (FIG. 1). FIG. 7A illustrates that the vacuum port 172 is fluidly connected to the tube inlet 78, and thus the lumen 76. Where included, the encapsulating body 44 provides on or more features such as compliant/flexible vacuum line to head-link assembly interface, secure mounting of the spreading mechanism 42 to the tube 40, masking of sharp or rough metallic features to prevent tissue abrasion, flexibility and compliance to allow spreading of the tube 40, and/or elasticity to assist in reversion of the tube 40 to a natural state following spreading. The encapsulating body 44 can assume other forms, and can be eliminated in other embodiments envisioned by the present disclosure.

Figure 8A:
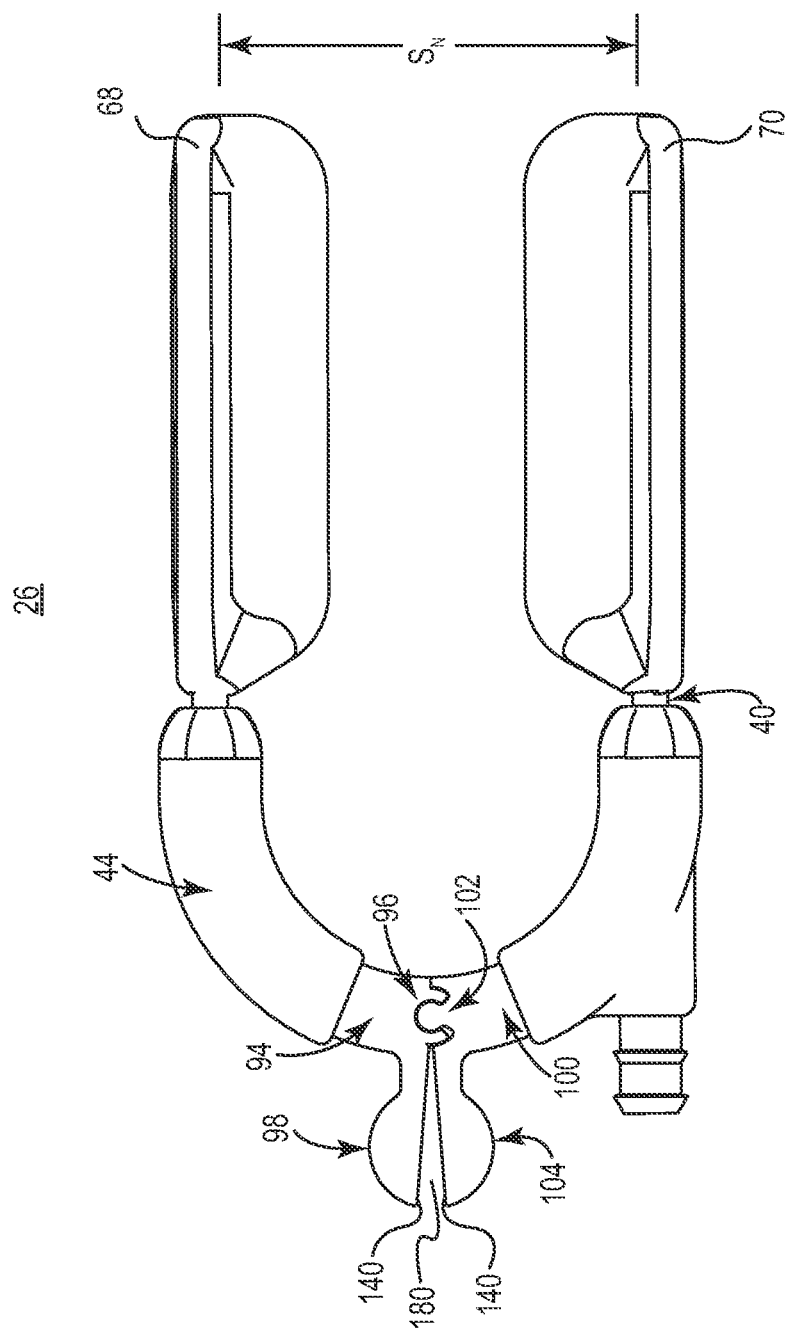
FIG. 8A illustrates a natural state of the head-link assembly of FIG. 2A.
Figure 8B:
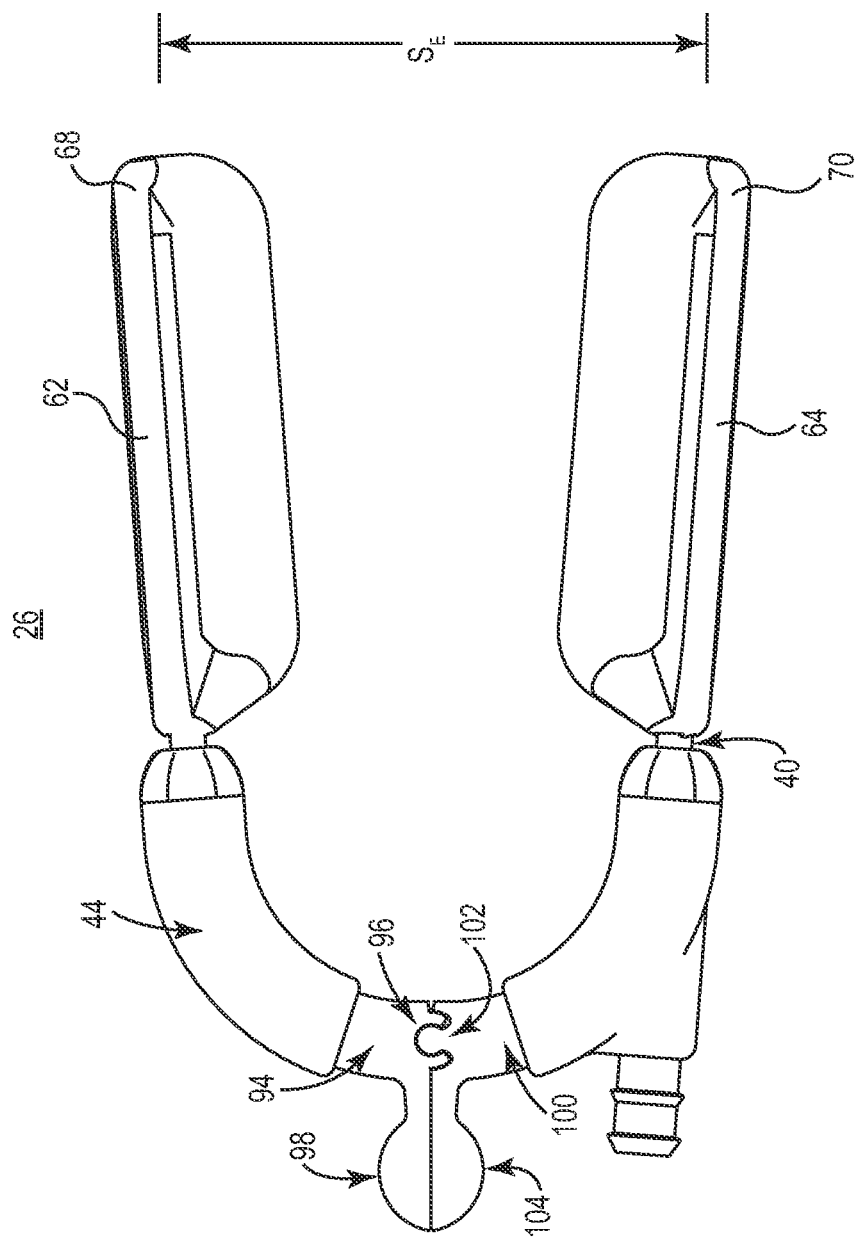
FIG. 8B illustrates an expanded state of the head-link assembly of FIG. 2A.

With reference to FIG. 8A, upon final construction, the head-link assembly 26 self-assumes a natural state in which the tips 68, 70 (hidden in the view, but referenced generally) are laterally spaced by the natural spacing $S_N$. The natural state, and in particular the natural spacing $S_N$, is dictated by the shape memory characteristic of the tube 40 and/or shape reinforcement characteristics imparted by the encapsulating body 44. Regardless, in the natural state, while the collet interface bodies 98, 104 are aligned in extension from the corresponding leg 94, 100, a tapered gap 180 is defined between the corresponding interior faces 140. The head-link assembly 26 can be transitioned to the expanded state of FIG. 8B by subjecting the collet interface bodies 98, 104 to a compressive force as described below. The compressive force brings the interior faces 140 into contact, or near contact, with one another along an entirety of the corresponding interface bodies 98, 104. The compressive force is, in turn, transferred to the corresponding legs 94, 100, causing the legs 94, 100 to pivot relative to one another via the hinge features 96, 102. Pivoting of the legs 94, 100 is translated onto the tube 40, causing the arms 62, 64 (hidden in the view, but referenced generally) to spread apart from one another, resulting in the expanded spacing $S_E$ between the tips 68, 70 in the expanded state. Upon removal of the external, compressive force, the head-link assembly 26 can self-transition back to the natural state of FIG. 8A, with the arms 62, 64 reverting back to the natural spacing $S_N$. The reversion back to the natural state can occur due to the shape memory characteristics of the tube 40 and/or an elasticity of the encapsulating body 44.

Returning to FIG. 1, the elongated arm 22 can assume various forms, and in some constructions is an articulating arm. For example, the articulating, elongated arm 22 can include a plurality of "ball and socket" links 200, and can be covered with a thin-walled elastomeric sheath. Some acceptable constructions of the articulating elongated arm 22 are described in U.S. Pat. No. 6,866,628 and U.S. Publication No. 2008/0139879, the entire teachings of both of which are incorporated herein by reference. In yet other embodiments, an articulating feature can be incorporated into the elongated arm 22 via constructions other than a "ball and socket" linkage. Alternatively, the elongated arm 22 can be a rigid tube or solid shaft.

Figure 9:
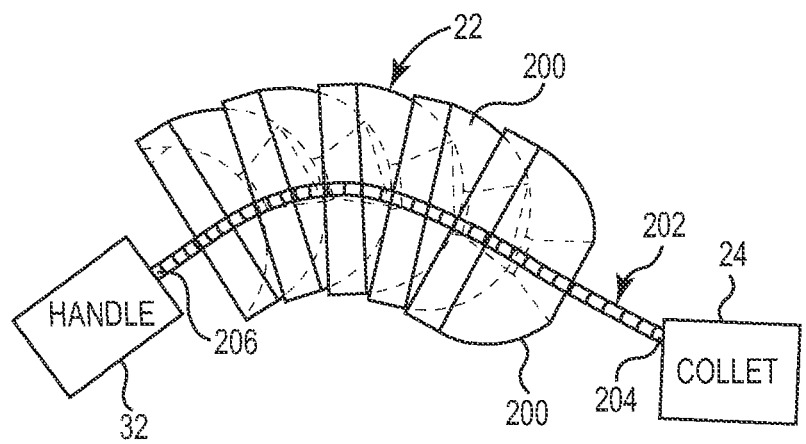
FIG. 9 illustrates, with portions in block form, a mechanism of operation of an elongated arm portion of the tissue stabilizer of FIG. 1.

Regardless of the exact construction of the elongated arm 22, a tension element 202, such as a cable, may be provided and extends through the elongated arm 22 as shown in FIG. 9. For example, the tension element 202 passes through the links 200 of the elongated arm 22, and is coupled at a distal end 204 to the collet 24 and at a proximal end 206 to the handle 32. As described in greater detail in the '628 patent and the '879 Publication, the tension element 202 can be placed into tension by rotation of the handle 32, that in turn causes proximal movement of the tension element 202, correspondingly tightening the components of the articulating arm 22, as well as stabilizing the location of the head-link assembly 26 (FIG. 1) relative to the collet 24. The tension element 202 can assume other forms, as can a relationship of the tension element 202 relative to the elongated arm 22. Regardless, the tissue stabilizer 20 incorporates one or more features that permit a user to effectuate tightening of the collet 24 as described below.

Figure 10:
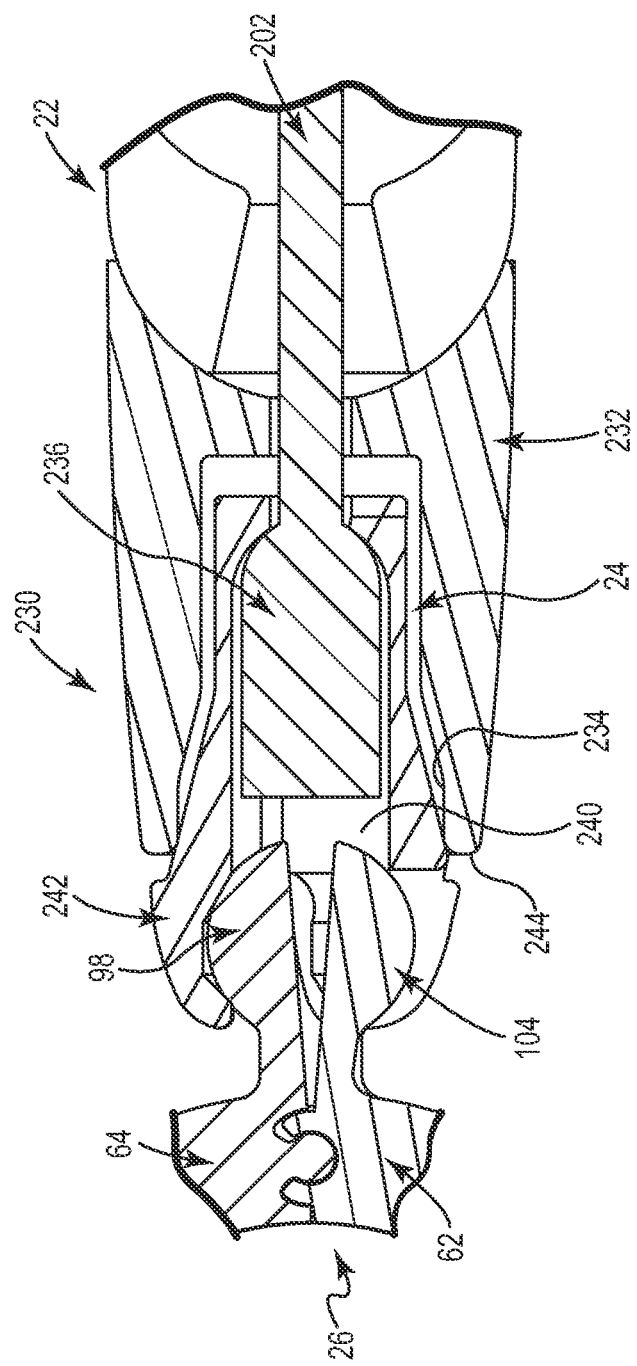
FIG. 10 is a cross-sectional view of a collet assembly portion of the tissue stabilizer of FIG. 1.

Returning to FIG. 1, the collet 24 can assume various forms, and can be provided as part of a collet assembly 230. For example, FIG. 10 illustrates one embodiment of the collet assembly 230 as including a collet receiving element 232, the collet 24, the tension element 202, and the collet interface bodies 98, 104 of the head-link assembly 26. In general terms, the collet 24 is slidably received within a bore 234 of the collet receiving element 232, and is connected to the tension element 202 (for example via a round-ended shank 236). The tension element 202, in turn, extends through a passage 238 in the collet receiving element 232. As a point of reference, the collet receiving element 232 can be assembled to, or be formed as part of, the elongated arm 22. The collet interface bodies 98, 104 are received within a cavity 240 defined by a head 242 of the collet 24. In the released state of FIG. 10, the head 242 is located distal a distal end 244 of the collet receiving element 232 such that the collet receiving element 232 does not apply an overt compressive force onto the head 242. Thus, the collet interface bodies 98, 104 remain slightly spaced from one another and can collectively freely rotate within the cavity 240.

The collet head 242 is radially collapsible from the normal diameter reflected in FIG. 10 that is otherwise greater than a diameter of the bore 234. The collet assembly 230 can be transitioned to a locked state by applying a tension or pulling force onto the tension element 202, thereby retracting the collet head 242 within the bore 234 of the collet receiving element 232. With this arrangement, the collet receiving element 232 applies a compressive force onto the collet head 242, that in turn forces the collet head 242 to compress onto the collet interface bodies 98, 104. As a result, a compressive force is applied to the collet interface bodies 98, 104, and the head-link assembly 26 is effectively spatially locked to the collet 24. Further, and as described above, this compressive force effectuates spreading of the head-link assembly arms 62, 64. The collet assembly 230 can assume other constructions differing from those described above. For example, in other constructions, the collet 24 can be coupled to the elongated arm 22 in a variety of other manners that may or may not entail the tension element 202 and/or the collet receiving element 232.

Returning to FIG. 1, the clamp 28 is generally constructed for selective attachment to a retractor (not shown) and thus can assume a variety of forms incorporating a clamp-like structure. The clamp 28 is designed to attach the tissue stabilizer 20 to conventional surgical retractors or other equipment located in a fixed relation to the operative site.

The turret 30, where provided, serves to effectuate rotation of the elongated arm 22 relative to the clamp 28. Exemplary, non-limiting descriptions of the turret 30 are provided in the '628 patent and the '879 Publication, the teachings of which are incorporated herein by reference. Other constructions are also envisioned. In yet other embodiments, the turret 30 can be omitted.

The handle 32 is shown in a highly stylized embodiment, but any device that performs the functions of a handle as described below can suffice. In general terms, the handle 32 provides for convenient handling of the tissue stabilizer 20 by a user, as well as user actuation of one or more of the tissue stabilizer 20 features. For example, with embodiments in which the elongated arm 22 is an articulating arm having a tension element extending therethrough, the handle 32 can be actuated (e.g., rotated) to fix the elongated arm 22 at a desired shape. Similarly, the handle 32 can be operated to effectuate locking and release of the collet 24 relative to the head-link assembly 26 as described above, as well as spreading of the head-link assembly arms 62, 64. Thus, the tissue stabilizer 20 provides an "automatic" spreading feature whereby a user simply actuates the handle 32 to prompt a self-transitioning of the head-link assembly 26 to the expanded state.

Finally, the vacuum tube assembly 34 can assume any form appropriate for delivering negative pressure or vacuum to the head-link assembly 26, and can include tubing 280 and a valve 282. Where provided, the valve is fluidly connectable to a source of negative pressure (not shown) and selectively fluidly connects the source of negative pressure with the tubing 280. The tubing 280, in turn, delivers the negative pressure to the head-link assembly 26 (e.g., via the vacuum port 172). In other constructions, the valve can be omitted.

Figure 11:
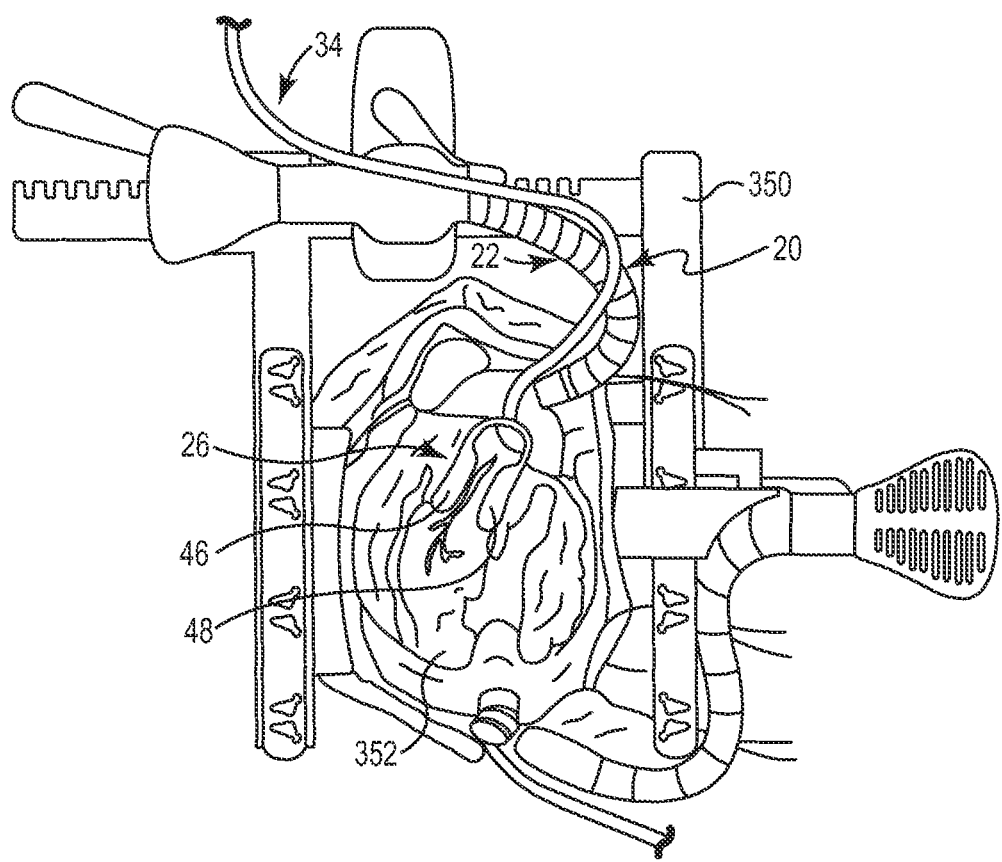
FIG. 11 is a perspective view illustrating use of the tissue stabilizer of FIG. 1 in a surgical field.

The tissue stabilizer 20 can be employed to perform various surgical procedures and/or portions of such procedures. As shown in FIG. 11, the tissue stabilizer 20 can be clamped or mounted to a sternal retractor 350, and employed to stabilize tissue of a patient's heart 352. For example, the head-link assembly 26 is initially mounted to the collet 24 (FIG. 1) in a manner permitting the head-link assembly 26 to freely rotate and pivot (in terms of yaw, pitch, and roll) relative to the collet 24 (and thus relative to the elongated arm 22) to virtually any spatial orientation implicated by the particular surgical site. Thus, the pod bodies 46, 48 can be arranged in various spatial orientations, such as a "toes up", "toes down", and/or "toes-to-the-side" positioning. Regardless, the head-link assembly 26 is in the natural state, with the tips 68, 70 (FIG. 8A) assuming the natural spacing $S_N$ (FIG. 8A). Once the head-link assembly 26 has been spatially oriented at a desired position, negative pressure is supplied to the head-link assembly 26 via the vacuum tube assembly 34. The negative pressure is delivered to the arms 62, 64 (FIG. 2A), establishing a suction force at the suction cups 80 (FIG. 2B). The suction, in turn, draws contacted tissue into engagement with the head-link assembly 26. The head-link assembly 26 is then transitioned to the expanded state described above, for example by applying a compressive force to the collet interface bodies 98, 104 (FIG. 2A) via the collet 24 as described above. With transitioning to the expanded state, the arms 62, 64 spread apart from one another (to the expanded spacing $S_E$ of FIG. 8B), thereby stretching the engaged tissue. Upon completion of the surgical procedure and cessation of the supply of negative pressure, the head-link assembly 26 is disengaged from the tissue. Further, upon removal of the compressive force placed upon the collet interface bodies 98, 104, the head-link assembly 26 self-reverts back to the natural state. The same procedure can be repeated at different locations of the heart 352 (e.g., multiple vessel grafting operations), with the head-link assembly 26 being repeatedly transitionable between the natural and expanded states.

The tissue stabilizers of the present disclosure provide a marked improvement over previous designs. The automatic pod spread feature is robust to abuse, and is highly predictable and repeatable. In some embodiments, the head-link assembly incorporates features for vacuum manifolding, assembly encapsulation, and flexibility and compliance for moving components. The sum of these features provides for a head-link assembly with automatic pod spread that is simplistic, low profile, extremely robust, very reliable, and easy to manufacture.

Figure 12:
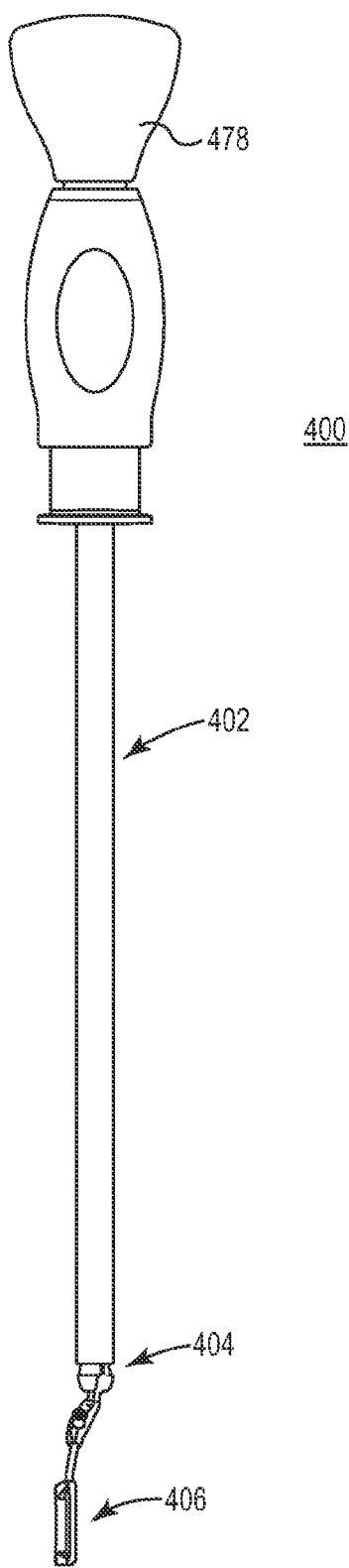
FIG. 12 is a side view of another tissue stabilizer in accordance with the present disclosure.

Another embodiment tissue stabilizer 400 is shown in FIG. 12. The tissue stabilizer 400 is akin to the tissue stabilizer 20 (FIG. 1) described above, and generally includes an elongated arm 402, a collet 404, and a head-link assembly 406. The collet 404 is disposed at a distal end of the elongated arm 402, and the head-link assembly 406 is rotatably coupled to the collet 404. Though not shown, a negative pressure source can be fluidly connected to the head-link assembly 406 for applying a suction force onto contacted tissue.

Unlike the elongated arm 22 (FIG. 1) described above that is optionally an articulating arm, the elongated arm 402 is a rigid member, and thus amenable for use in minimally invasive procedures (e.g., direct vision thoractomy). The elongated arm 402 can be a tubular member formed of a rigid material such as steel.

Figure 13:
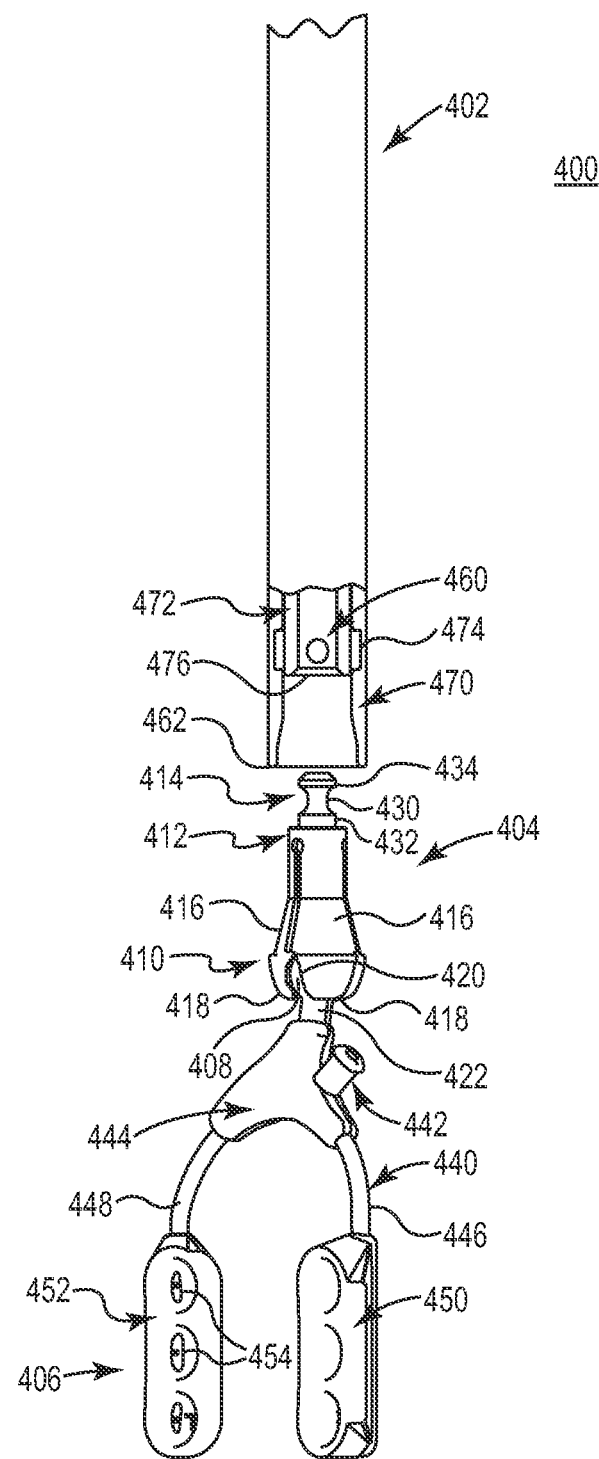
FIG. 13 is a perspective, exploded view of the tissue stabilizer of FIG. 12, with portions shown in cross-section.

As best shown in FIG. 13, the tissue stabilizer 400 is constructed such that the collet 404 is permanently associated with the head-link assembly 406, and is removably connected with the elongated arm 402. With this in mind, the collet 404 includes or forms a head 410, a shoulder 412, and a tang 414. The head 410 is configured to rotatably receive a spherical member 408 of the head-link assembly 406 as described below, and generally defines a cavity (hidden in the view of FIG. 13). In some constructions, the head 410 is defined by a plurality of spaced apart fingers 416 extending from the shoulder 412 to a distal end 418. The fingers 416 are radially deflectable relative to one another, pivoting at the shoulder 412. While a collective diameter defined at the distal ends 418 is sized to retain the spherical member 408 of the head-link assembly 406 in a natural state of the collet 402, the spherical member 408 is freely rotatable within the head 410. When subjected to an external compressive force, the fingers 416 deflect radially inwardly toward one another to more rigidly engage the spherical member 408 in a locked state as described below. To facilitate a more complete range of motion of the head-link assembly 406 relative to the collet 404, enlarged gaps 420 (one of which is shown in FIG. 13) can be defined between adjacent ones of the fingers 416 at the distal end 418. The gaps 420 are sized to permit passage of a shaft component 422 of the head link assembly 406.

The tang 414 extends from the shoulder 412 in a direction opposite the head 410, and is configured for connection with the elongated arm 402. In some constructions, the tang 414 defines a circumferential groove 430 between a leading side 432 and a trailing side 434 thereof. The circumferential groove 430 has a rounded curvature for reasons made clear below. Regardless, a diameter of the tang 414 along the groove 430 is less than a diameter of the leading side 432 and of the trailing side 434.

The head-link assembly 406 can have a wide variety of forms, and in some constructions includes a tube 440, a port 442, and a frame 444 maintaining the shaft 422 and the spherical member 408 as described above. The tube 440 forms or defines opposing arms 446, 448 to which a pod body 450, 452 is mounted, respectively. In some embodiments, the tube 440 forms a single lumen (hidden) that is fluidly connected to orifices 454 formed in each of the arms 446, 448 and fluidly connected to the corresponding pod body 450, 452. The port 442, in turn, is fluidly connected to the lumen and establishes a connection point to separate vacuum tubing (not shown). In other embodiments, a separate lumen can be discretely established for each of the arms 446, 448. Regardless, the tube 440, and in particular the arms 446, 448, can be formed of a malleable yet rigid material (e.g., steel) that allows a user to manipulate the arms 446, 448 (and thus the pod bodies 450, 452) to desired spatial orientations relative to one another.

The frame 444 extends from the tube 440 in a direction opposite the arms 446, 448, and serves to displace or space the tube 440 from the spherical member 408. The frame 444 can be embedded within a protective covering. In other embodiments, the frame 444 can be omitted.

Unlike the head-link assembly 26 (FIG. 1) described above, the head-link assembly 406 of the tissue stabilizer 400 need not necessarily incorporate an automatic spreading feature. Thus, for example, the spreading mechanism 42 (FIG. 2A) described above, may or may not be assembled to the tube 440.

A variety of constructions can be employed to effectuate coupling of the collet 404 with the elongated arm 402. For example, in some constructions, the elongated arm 402 can include a ball bearing assembly 460 (referenced generally) adjacent a distal end 462, with the ball bearing assembly 460 rotatably capturing the tang 414 via the circumferential groove 430. The elongated arm 402 is further configured to facilitate selective connection and disconnection of the collet 404. For example, the elongated arm 402 can include an outer tube 470 and an inner shaft 472. The outer tube 470 forms an internal release aperture 474 adjacent the distal end 462. The inner shaft 472 is slidably retained within the outer tube 470, with the ball bearing assembly 460 retained at a leading end 476 thereof. A trailing end (not shown) extends through the outer tube 470 and is coupled to an actuator, such as a handle 478 as shown in FIG. 12. With this construction, a user can longitudinally move the inner shaft 472 relative to the outer tube 470 via operation of the handle 478.

Figure 14A:
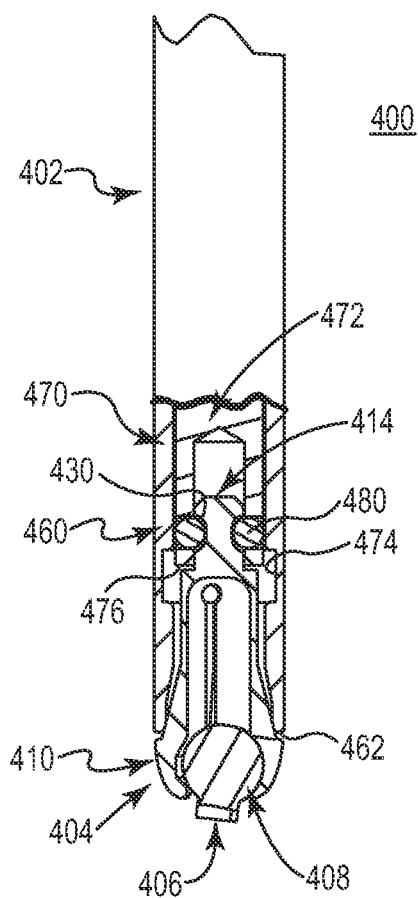
FIG. 14A is a partial, cross-sectional view of a portion of the tissue stabilizer of FIG. 12 in a connected, translatable condition.
Figure 14B:
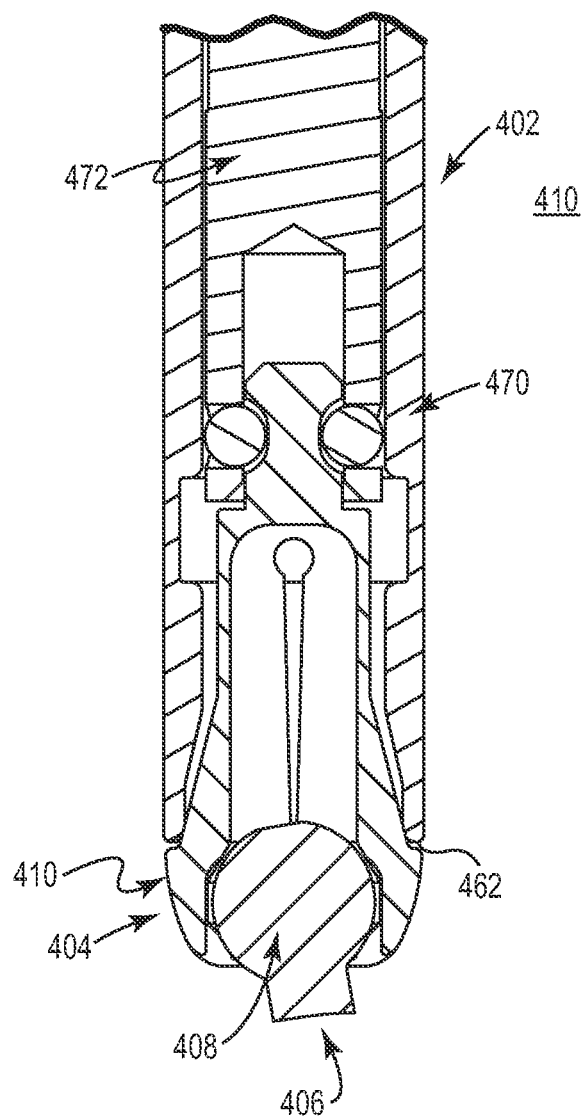
FIG. 14B is a cross-sectional view of a portion of the tissue stabilizer of FIG. 12 in a connected, locked condition.

With the above construction, the collet 404 can be connected to the arm 402 in the translatable condition reflected by FIG. 14A in which the tang 414 of the collet 404 is coupled to the ball bearing assembly 460, and the leading end 476 of the inner shaft 472 is retracted within the outer tube 470. The release aperture 474 is longitudinally displaced from the ball bearing assembly 460 such that ball bearings 480 of the assembly 460 are directed into the groove 430. As a result, the tang 414 is captured relative to the elongated arm 402. However, in the translatable condition, the distal end 462 of the outer tube 470 is proximally displaced from the collet head 410 such that minimal, if any, compressive force is applied by the arm 402 onto the collet head 410, with the collet head 410, in turn, minimally compressing on to the spherical member 408. Thus, the head-link assembly 406 can freely pivot and rotate (yaw, pitch, and roll) relative to the collet 404, allowing a user to select a desired spatial orientation. Once the desired orientation of the head-link assembly 406 has been achieved, the arm 402/collet 404 connection is transitioned to the locked condition of FIG. 14B by retracting the inner shaft 472 relative to the outer tube 470 and/or distally advancing the outer tube 470 relative to the inner shaft 472. For example, in some constructions, the handle 478 (FIG. 12) can be rotated to effectuate a slight retraction of the inner shaft 472. Regardless, as the inner shaft 472 is retracted, the collet 404 is similarly retracted proximally relative to the outer tube 470, with the distal end 462 of the outer tube 470 thus applying a more overt compressive force onto the collet head 410. In the locked state, then, the outer tube 470 compresses the head 410 on to the spherical member 408, thereby locking the head-link assembly 406 at the selected spatial orientation.

Figure 14C:
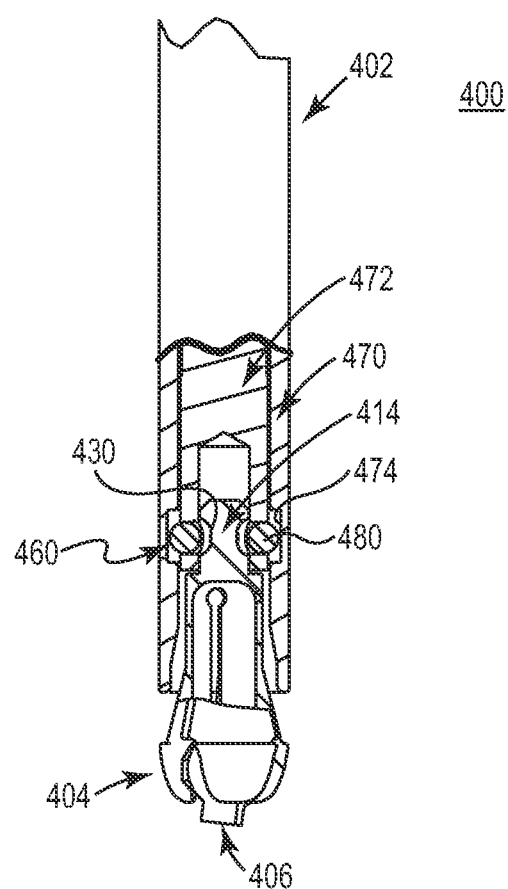
FIG. 14C is a partial, cross-sectional view of a portion of the tissue stabilizer of FIG. 12 in a release condition.

When desired, the collet 404 can be disconnected from the arm 402 by transitioning the arm 402 to the release condition of FIG. 14C. In particular, the inner shaft 472 is distally advanced relative to the outer tube 470 until the ball bearing assembly 460 is longitudinally aligned with the release aperture 474. The release aperture 474 is sized to partially receive the ball bearings 480, allowing the ball bearings 480 to disengage or release from the tang groove 430. In the release condition, a user can simply pull the tang 414 outwardly from the ball bearing assembly 460, thereby disconnecting the collet 404/head-link assembly 406 from the elongated arm 402. Re-connection of the collet 404/head-link assembly 406 to the elongated arm 402 can be accomplished in a reverse manner.

The tissue stabilizer 400 as described above is highly conducive to surgical procedures in which a quick disconnect of the head-link assembly 406 is beneficial For example, the tissue stabilizer 400 can be employed with minimally invasive (e.g., direct vision thoracotomy) coronary artery bypass graft procedures. The flexibility and ease of connection of the head-link assembly 406 within a tight space via the quick-connect/disconnect configuration described above provides a marked advantage over previous designs.

Although the present disclosure has been described with reference to preferred embodiments, workers skilled in the art will recognize that changes can be made in form and detail without departing from the spirit and scope of the present disclosure.

What is claimed is:

1. A tissue stabilizer comprising:
   (i) an elongated arm terminating at a distal end and including an outer tube and an inner shaft, the inner shaft slidably disposed within the outer tube;
   (ii) a collet disposed at the distal end and releasably connected to the elongated arm, the collet including:
      a head having a cavity defined by a plurality of spaced-apart fingers, and
      a tang releasably engageable with the elongated arm;
   wherein the tissue stabilizer is configured to provide:
      a first condition in which the tang is attached to the inner shaft while the inner shaft is within the outer tube, and
      a second condition in which the tang is detached from the inner shaft and the collet is removable from an entirety of the elongated arm while the inner shaft is within the outer tube; and
   (iii) a head-link assembly rotatably coupled to the collet, the head-link assembly including:
      a spherical member retained within the head of the collet, and
      a tube for applying negative pressure to tissue, the tube defining an intermediate section and opposing first and second arms extending from the intermediate section;
   wherein the head-link assembly is transitionable from an unlocked state in which the spherical member is freely rotatable within the head of the collet and a locked state in which the fingers of the collet are deflected radially inward relative to the unlocked state by a compressive force, thereby causing the fingers to rigidly engage the spherical member and hold the head-link assembly in a fixed position.

2. The tissue stabilizer of claim 1, wherein the tube is U-shaped.

3. The tissue stabilizer of claim 2, wherein the elongated arm further comprises a ball bearing assembly retained at a leading edge of the inner shaft.

4. The tissue stabilizer of claim 3, wherein the tang of the collet comprises a groove that engages with the ball bearing assembly to releasably connect the collet to the elongated arm.

5. The tissue stabilizer of claim 3, wherein the outer tube forms an internal release aperture defining a diameter greater than an inner diameter of the outer tube proximal the internal release aperture, and further wherein the elongated arm is configured to provide:
- a translatable condition in which the tang is engaged with the inner shaft and the ball bearing assembly is proximal to the internal release aperture; and
- a release condition in which the ball bearing assembly is within the internal release aperture to permit release of the tang from the inner shaft.

6. The tissue stabilizer of claim 1, wherein the tube is metal.

7. The tissue stabilizer of claim 1, wherein each of the arms forms a plurality of vacuum orifices.

8. The tissue stabilizer of claim 7, wherein the tube forms a continuous lumen fluidly connected to each of the vacuum orifices.

9. The tissue stabilizer of claim 8, wherein the intermediate section forms a single inlet port for fluidly connecting a source of negative pressure with the lumen.

10. The tissue stabilizer of claim 7, wherein the head-link assembly further comprises a first pod body mounted to the first arm and a second pod body mounted to the second arm.

11. The tissue stabilizer of claim 10, wherein at least one of the pod bodies is formed of a polymer that defines a plurality of cups each of which is fluidly connected to the respective vacuum orifice in the corresponding arm.

12. The tissue stabilizer of claim 1, wherein the tissue stabilizer is configured such that the head-link assembly remains captured to the collet when the collet is disconnected and separated from the elongated arm.

13. The tissue stabilizer of claim 12, wherein the tissue stabilizer is configured such that the tang is brought into engagement with the inner shaft by advancing the tang proximally through an opening at a distal tip of the outer tube.

14. The tissue stabilizer of claim 13, wherein the tissue stabilizer is configured such that the tang is released from the elongated arm by pulling the tang distally through the opening at the distal tip of the outer tube.

* * * * *